United States Patent [19]

Igushi et al.

[11] Patent Number: 5,185,641
[45] Date of Patent: * Feb. 9, 1993

[54] APPARATUS FOR SIMULTANEOUSLY MEASURING LARGE AND SMALL PARTICLE SIZE DISTRIBUTION

[75] Inventors: Tatsuo Igushi; Yoshiaki Togawa, both of Kyoto, Japan

[73] Assignee: Horiba, Ltd., Kyoto, Japan

[*] Notice: The portion of the term of this patent subsequent to Nov. 17, 2009 has been disclaimed.

[21] Appl. No.: 786,553

[22] Filed: Nov. 1, 1991

[30] Foreign Application Priority Data

Nov. 3, 1990 [JP] Japan .................................. 2-297869
Nov. 17, 1990 [JP] Japan .................................. 2-312251

[51] Int. Cl.⁵ .......................................... G01N 15/02
[52] U.S. Cl. .................................... 356/336; 356/343
[58] Field of Search ....................... 356/336, 338, 343; 250/573

[56] References Cited

U.S. PATENT DOCUMENTS 3,724,951  4/1973  Seelbinder ............................ 356/336
4,482,247  11/1984  Meltz et al. ........................... 356/343
4,541,719  9/1985  Wyatt ................................... 356/343
4,679,939  7/1987  Curry et al. ........................... 356/336
4,781,460  11/1988  Bott ..................................... 356/338
5,017,008  5/1991  Akiyama .............................. 356/336
5,105,093  4/1992  Niwa .................................... 356/336

FOREIGN PATENT DOCUMENTS

44645    2/1987  Japan ................................... 356/336
115950   5/1991  Japan ................................... 356/336

Primary Examiner—Richard A. Rosenberger
Attorney, Agent, or Firm—Price, Gess & Ubell

[57] ABSTRACT

An apparatus for measuring a wide range of particle sizes in of a sample fluid with two separate light sources is provided. The individual light sources can be compensated to take into account any variations in transmission factors through the sample fluid prior to calculating the particle size distribution. Additionally, any fluctuations in the light source can also be measured to provide a compensation factor for the measured light intensities.

7 Claims, 7 Drawing Sheets

APPARATUS FOR SIMULTANEOUSLY MEASURING LARGE AND SMALL PARTICLE SIZE DISTRIBUTION

BACKGROUND OF THE INVENTION

1. Field of the Invention

The present invention relates to an apparatus for measuring a particle size distribution and more particularly a particle size distribution of a wide range of sample particles is measured by utilizing a diffraction phenomenon or a scattering phenomenon brought about by irradiating dispersed particles with different sources of light.

2. Description of Related Art

In an apparatus for measuring a particle size distribution utilizing a diffraction phenomenon or a scattering phenomenon of a light by particles, an intensity distribution of a diffracted light or scattered light is measured and then the resulting relationship is subjected to a calculation operation based on the theory of Fraunhofer diffraction or Mie scattering to calculate a particle size distribution of sample particles.

Figure 8:
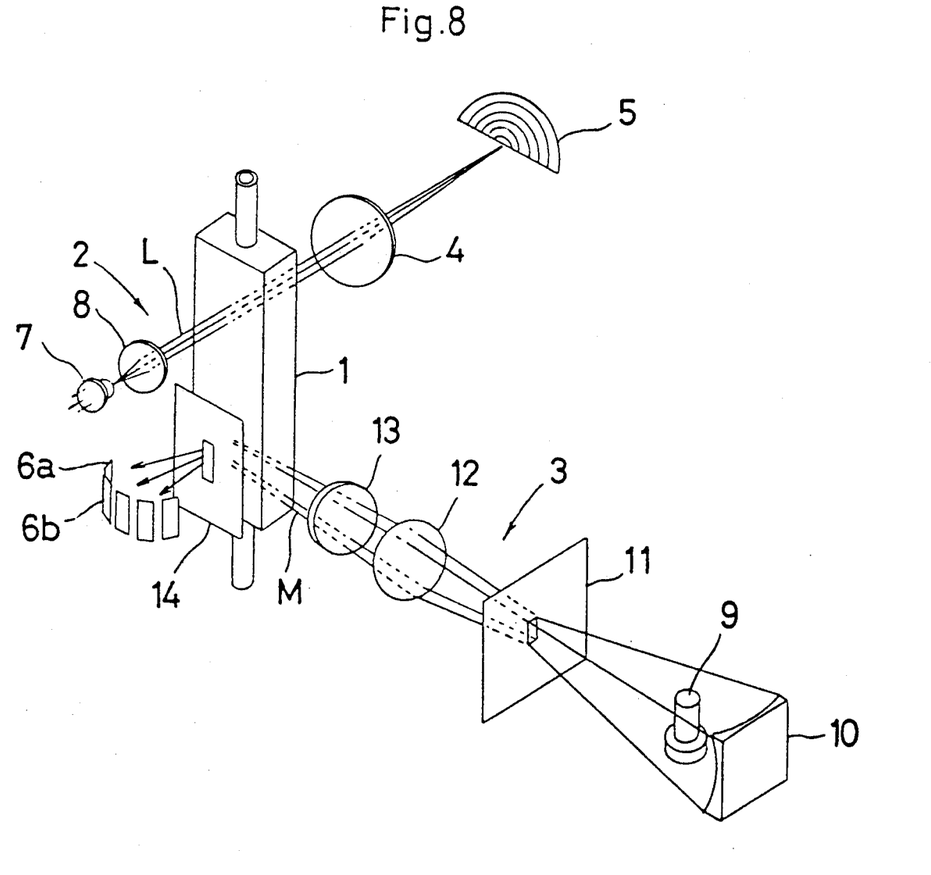
FIG. 8 is a perspective view showing a construction of the conventional apparatus for measuring a particle size distribution.

FIG. 8 is a perspective view showing a conventional example of an apparatus for measuring a particle size distribution of this type. Referring to FIG. 8, a flow cell 1 is a transparent vessel through which a medium with sample particles dispersed therein flows. The flow cell 1 is irradiated with parallel laser beams L from a laser optical system 2. Separately from the parallel laser beams L, the flow cell 1 is also irradiated with wavelength beams M of a substantial single frequency from a single wavelength optical system 3.

The laser beams L, which have been diffracted or scattered by the sample particles within the flow cell 1, are incident upon a ring-shaped photosensor array 5 through a Fourier transformation lens 4 to determine a particle size distribution of the sample particles. This is effective in determining larger particle diameters from the resulting distribution of the light intensity which is measured.

In addition, single wavelength beams M, which have been diffracted or scattered by the sample particles in the same manner, are incident upon a plurality of photosensors 6a, 6b, etc., which are arranged at spaced positions. These positions correspond to scattering angles different from each other relative to the flow cell 1, to determine a particle size distribution of the sample particles having relatively smaller particle diameters from a distribution of the measured light intensity.

In addition, referring to FIG. 8 again, reference numeral 7 designates a laser diode, reference numeral 8 designates a collimator lens, reference numeral 9 designates a light source, reference numeral 10 designates a spherical mirror, reference numeral 12 designates a collecting lens, reference numeral 13 designates an interference filter, and reference numeral 14 designates a light-measuring slit.

With the above described apparatus for measuring particle size distribution, the laser beams L from the laser optical system 2 and the monochrome beams M from the optical system 3 are incident upon the same flow cell 1 to make the laser beams, which have been diffracted or scattered by the sample particles within the flow cell 1, incident upon the ring-shaped photosensor array 5, and simultaneously make the monochrome beams M, which have been diffracted or scattered by the sample particles, incident upon a plurality of photosensors 6a, 6b. As a result, the particle size distribution of the sample particles having relatively larger particle diameters is measured by the laser beams L, while the particle size distribution of the sample particles having relatively smaller particle diameters is measured by the monochrome beams M. Accordingly, an advantage occurs in that the particle size distribution ranging from smaller particle diameters to larger particle diameters can be measured by means of a single apparatus However, in the above described conventional apparatus for measuring a particle size distribution, if a concentration of sample particles flowing through the flow cell 1 is changed, then the optical intensity measured by means of the ring-shaped photosensor array 5 and a plurality of photosensors 6a, 6b is also changed, depending upon the change of the concentration of sample particles. That is to say, there is a tendency that the incident light, which has been diffracted or scattered by the sample particles, is more strongly influenced by a multiple scattering with an increase in concentration of sample particles and thus the optical intensity received by the ring-shaped photosensor array 5 and the photosensors 6a, 6b is reduced.

In particular, in the case where the particles have diameters of a submicron order, the multiple scattering can be changed depending upon the wavelength of the irradiated beams, so that an influence of the multiple scattering upon the optical intensity of the laser beams measured by the ring-shaped photosensor array 5 is different from that upon the optical intensity of the monochrome beams measured by a plurality of photosensors 6a, 6b.

However, in the case of the conventional apparatus for measuring a particle size distribution, the influence of the concentration of sample particles upon the measured results has not been taken into consideration, so that problems have occurred in that the measured results are different, depending upon the concentration of sample particles flowing through the flow cell 1 even though the sample particles have the same particle size distribution.

In addition, if a quantity of laser beams emitted from the laser diode 7 and the light source 9, which is a light source of the laser optical system 2 and the single wavelength optical system 3, respectively, fluctuates, then the quantity of light received by the ring-shaped photosensor array 5 and the photosensors 6a, 6b dependently fluctuates so that a problem occurs in that the particle size distribution cannot be accurately determined.

SUMMARY OF THE INVENTION

It is a first object of the present invention to provide an apparatus for measuring a particle size distribution capable of accurately measuring particle size distribution without being influenced by any variation in a concentration of sample particles.

It is a second object of the present invention to provide an apparatus for measuring a particle size distribution capable of accurately measuring a particle size with a quantity of light emitted from a light source.

In order the achieve the first object, a larger diameter particle-detecting optical system containing laser beam-irradiating means for irradiating a sample vessel, in which a medium with sample particles dispersed is housed, generates laser beams. A ring-shaped detector measures the optical intensities of the laser beams having respective scattering angles diffracted or scattered by the sample particles. A smaller particle-detecting optical system includes a single wavelength light-irradiating means for irradiating the sample vessel with single wavelength light obtained from a lamp light and a group of photosensors measure the optical intensities of the single wavelength light at respective scattering angles diffracted or scattered by the sample particles. A first transmitted beam-measuring photosensor for measuring an optical intensity of a laser beam, transmitted through the sample vessel without being diffracted or scattered by the sample particles, is provided. A second transmitted beam-measuring photosensor for measuring an optical intensity of a single wavelength light transmitted through the sample vessel without being diffracted or scattered by the sample particles is also provided. Compensating means for calculating a transmission factor of the laser beam and that of the single wavelength light, respectively, on the basis of data measured by a first transmitted beam-measuring photosensor and a second transmitted beam-measuring photosensor is used to compensate the data photosensors. Finally, a particle size distribution-calculating means is used to calculate a particle size distribution of the sample particles from the compensated data on the basis of the theory of Fraunhofer diffraction or Mie scattering.

The data measured by means of the ring-shaped detector for measuring the optical intensities of the laser beams diffracted or scattered by the sample particles and the data measured by means of the group of photosensors for measuring the optical intensities of the monochrome light are compensated by means of the compensating means by a quantity corresponding to a concentration of sample particles at that time and the particle size distribution of the sample particles is calculated by means of the particle size distribution-calculating means on the basis of the compensated data of measurement. Accordingly, a determined particle size distribution can be correctly achieved.

A larger diameter particle-detecting optical system containing a laser beam-irradiating means for irradiating a sample vessel, in which a medium with sample particles dispersed is housed, generates laser beams. A ring-shaped detector measures the optical intensities of the laser beams having respective scattering angles diffracted or scattered by the sample particles. A smaller particle-detecting optical system contains a single wavelength light-irradiating means for irradiating the sample vessel with monochrome light is obtained from a lamp source and a group of photosensors for measuring optical intensities of monochrome light having the respective scattering angles diffracted or scattered by the sample particles. A first beam splitter is provided for separating a portion of the laser beams before they are incident upon the sample vessel. A first monitoring photosensor for measuring an optical intensity of the laser beams is separated by means of the first beam splitter. A second beam splitter is provided for separating a part of the monochrome light before they are incident upon the sample vessel. A second monitoring photosensor for measuring an optical intensity of the monochrome light separated by means of the second beam splitter are provided. A data input circuit for putting in data measured by the ring-shaped detector, data measured by the group of photosensors, and data measured by the respective monitoring photosensors is utilized. A compensating means for compensating for data is measured by the ring-shaped detector and the group of photosensors, depending upon the data measured by the respective monitoring photosensors at a point of time when the above described data are measured. Particle size distribution-calculating means calculates a particle size distribution of the sample particles from the compensated data of measurement on the basis of the theory of the Fraunhofer diffraction or the Mie scattering.

According to the above described construction, the data measured by the ring-shaped detector for measuring the optical intensities of the laser beams diffracted or scattered by the sample particles and the data measured by the group of photosensors for measuring the optical intensities of the monochrome light are compensated by the compensating means by a quantity corresponding to an optical quantity of the laser beams measured by the first monitoring photosensor and an optical quantity of the monochrome light measured by the second monitoring photosensor at a point of time when the data measured by the ring-shaped detector and the data measured by the group of photosensors are measured and the particle size distribution of the sample particles is accurately calculated by the particle size distribution-calculating means on the basis of the compensated data of measurement.

In addition, the data measured by the larger diameter particle-detecting optical system and the data measured by the smaller diameter particle-detecting optical system are used as data for the particle size distribution-calculating means by means of the data input circuit, so that a wide range of particle sizes from smaller particle diameters to larger particle diameters can be simply measured in a single measurement operation.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

One preferred embodiment of the invention is shown in FIGS. 1 to 4, in which.

A second preferred embodiment of the invention is shown in FIGS. 5 to 7, in which.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein distribution apparatus.

The preferred embodiments of the present invention will be below described with reference to the drawings.

Figure 1:
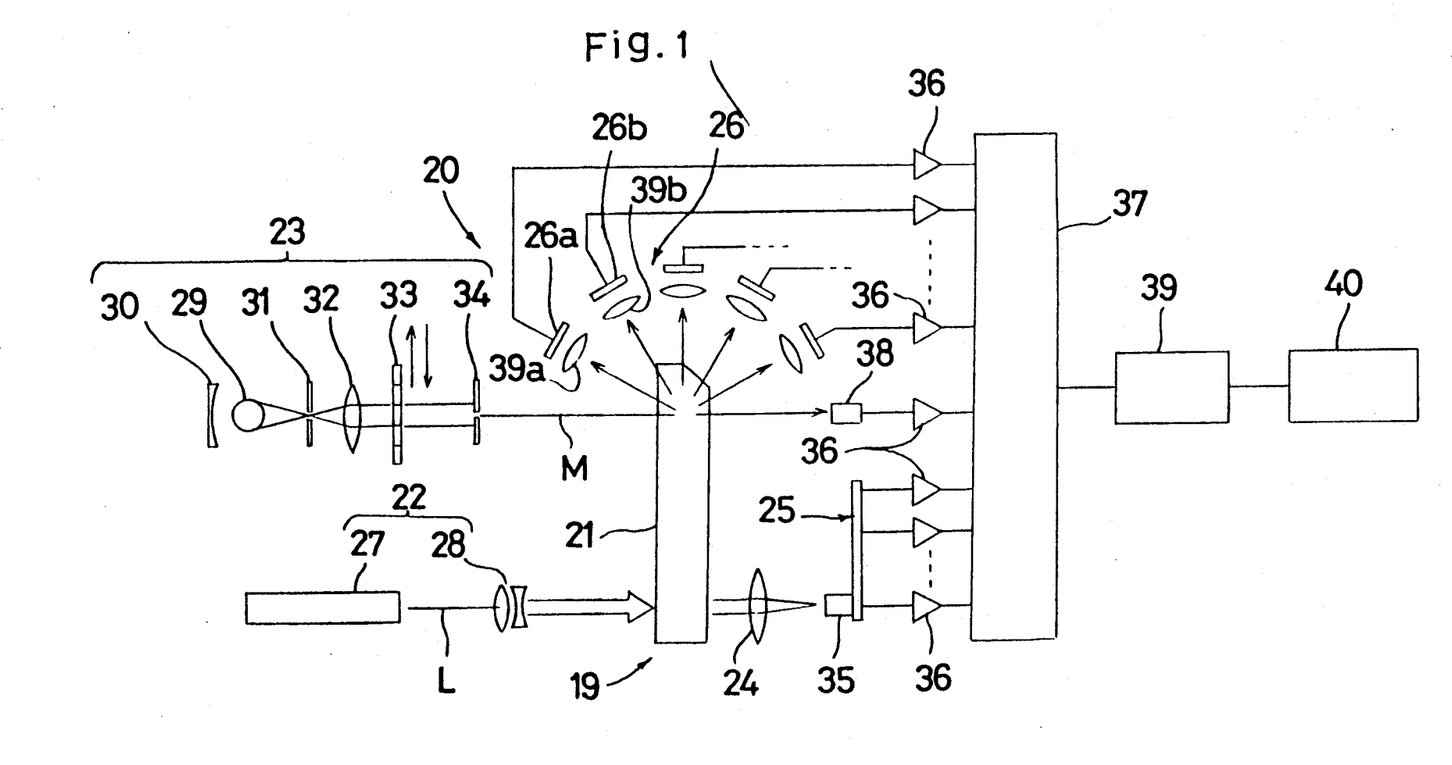
FIG. 1 is a diagram schematically showing an outline of an apparatus for measuring a particle size distribution.

FIG. 1 is a diagram showing an optical measuring system in an apparatus for measuring a particle size distribution with a range of 0.04 μm to 1 mm according to a first embodiment. A sample cell 21 is a transparent vessel housing a sample liquid with sample particles dispersed in a medium therein and laser beam-emitting means 22 is an optical system for irradiating the sample cell 21 with parallel laser beams L along an optical axis. The laser beam-emitting means 22 is composed of a laser beam source 27, such as a HeNe laser for emitting parallel laser beams L and a beam expander 28 for expanding a flux of the laser beams L. The sample cell 21 is shown with a bevelled upper configuration to improve the transmission of diffracted or scattered laser beams at larger angles.

A collecting lens 24 for collecting the laser beams L, diffracted or scattered by the sample particles and the laser beams L directly transmitted through the sample cell 21 without being diffracted or scattered by the sample particles on a ring-shaped detector 25, is arranged on an optical axis of the laser beam-emitting means 22 in front of the sample cell 21.

The ring-shaped detector 25 is further arranged in front of the collecting lens 24 for receiving the laser beams at respective scattering angles after being diffracted or scattered by the sample particles to measure their optical intensity distribution.

Figure 2:
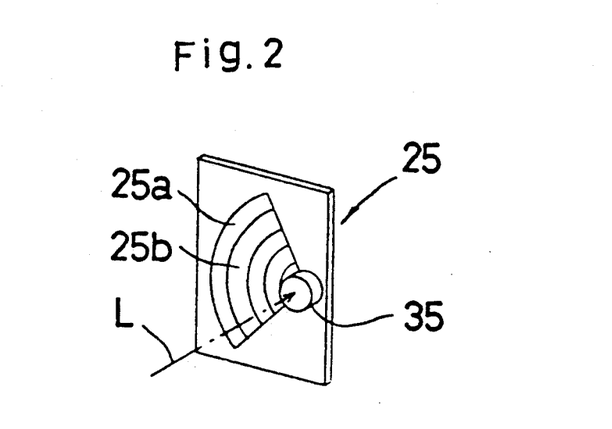
FIG. 2 is a perspective view showing a ring-shaped detector used in the apparatus for measuring a particle size distribution shown in FIG. 1.

FIG. 2 is a perspective view showing a construction of the ring-shaped detector 25. This ring-shaped detector 25 is composed of a plurality of scattered beam photosensors, such as elements 25a, 25b, divided into a ring shape with the optical axis of the laser beam-emitting means 22 positioned at a center for detecting the laser beams L, diffracted or scattered by the sample particles at the respective angles off of the optical axis, depending upon the diameters of the sample particles. In addition, one transmitted beam photosensor 35 is arranged at a central position of the ring-shaped detector 25 for detecting those laser beams L transmitting through the sample cell 21 without being diffracted or scattered. The respective photosensors 25a, 25b and 35 of the ring-shaped detector 25 are connected with a multiplexer 37 through respective amplifiers 36, corresponding thereto.

The laser beam-emitting means 22, the collecting lens 24 and the ring-shaped detector 25 compose a larger diameter particle-detecting optical system 19 for receiving the laser beams diffracted or scattered by sample particles having relatively larger particle diameters.

Single wavelength light-emitting means 23 is an optical system for irradiating the sample cell 21 with substantially a single wavelength light M having a wavelength shorter than those of the laser beams L and composed of a lamp light source 29, a spherical mirror 20, apertures 31, 34, a collimator lens 32, and an interference filter 33.

The spherical mirror 30 is a mirror for collecting light emitted backward from the lamp light source 29 on the aperture 31, arranged in front of the lamp light source 29. The aperture 31 contracts the light from the lamp light source 29 to form a sufficiently small bundle of beams.

The collimator lens 32, arranged in front of the aperture 31, is a lens for converting the lamp light, which has been contracted by means of the aperture 31, into parallel beams. The interference filter 33, arranged in front of the collimator lens 32, is a filter for taking out merely beams M having an appointed monochrome range from the parallel beams.

Figure 3:
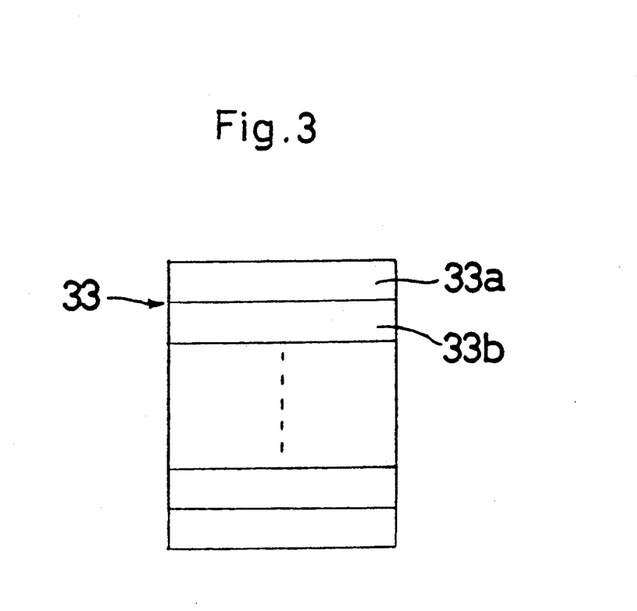
FIG. 3 is a plan view showing an interference filter used in the apparatus for measuring a particle size distribution.

FIG. 3 is a plan view showing a construction of the interference filter 33. The interference filter 33 is composed of a plurality of, for example, ¼ wavelength plates 33a, 33b, etc., different in transmitting wavelength longitudinally arranged so that the beams M, having an appointed single wavelength, may be switched by to a plurality of steps in respective wavelength ranges by shifting the position of the interference filter 33 up or down.

The aperture 34, arranged in front of the interference filter 33, provides a contraction of a bundle of the single wavelength beams M from the interference filter 33. The single wavelength beams M, which have passed through the aperture 34, are incident upon a position different from the incident position of the laser beams L of the sample cell 21.

In addition, a transmitted beam photosensor 38 for detecting the single wavelength beams M, which have been transmitted through the sample cell 21 without being diffracted or scattered by the sample particles, is arranged on an optical axis of the single wavelength beam-emitting means 23 at the rear of the sample cell 21. The photosensor 38 is connected with a multiplexer 37 through an amplifier 36, corresponding thereto.

A plurality of photosensors, such as elements 26a, 26b, comprising a group of photosensors 26 for individually detecting the monochrome beams M, diffracted or scattered by the sample particles, are arranged at respective predetermined scattering angle positions. In particular, the photosensors 26a, 26b are arranged not only on a side in the rear of the sample cell 21, in short, the side on which the monochrome-emitting means 23 is arranged, but also on a side in front of the sample cell 21 to measure an optical intensity also for the monochrome beams M scattered ahead of the sample cell 21. The respective photosensors 26a, 26b receive the respective diffracted or scattered beams collected by means of collecting lenses 39a, 39b, corresponding thereto. The photosensors 26a, 26b are connected with the multiplexer 37 through amplifiers 36, corresponding thereto.

The monochrome-emitting means 23, the group of comprise a small diameter particle-detecting optical system 20 for receiving beams diffracted or scattered by the sample particles having relatively smaller particle diameters.

The multiplexer 37 is a circuit having a function of taking in data of optical intensity detected by means of the photosensors 25a, 25b, etc., and 35, of the ring-shaped detector 25 and data detected by the other photosensors 26a, 26b, etc., and 38 in an appointed order and converting the data into a series of signals relative to the taking-in order to send them to an A/D convertor 39. The A/D convertor 39 is a circuit for converting the data of measurement, in short, analog data, into digital data and the digital data is sent to an operating device 40.

The operating device 40 is a device for conducting a computational operation of determining a particle size distribution of the sample particles within the sample cell 21 on the basis of the digital data on optical intensity and can include a computer and appropriate software. This operation determines the particle size distribution on the basis of a software program algorithm applying the theory of the Fraunhofer diffraction or the Mie scattering (as known in the art), but can also include a compensating function for initially compensating the inputted data used for the operation prior to the calculation of the particle size distribution.

That is to say, compensation in this case compensates the data of optical intensity detected by means of the photosensors 25a, 25b, 26a, 26b on the basis of data on the transmitted beams received by the transmitted beam photosensors 35, 38 when the diffracted beams or the scattered beams are received by the respective photosensors 25a, 25b, 26a, 26b. The data measured by the photosensors 25a, 25b receiving the diffracted beams or the scattered beams of the laser beams L are thereby compensated on the basis of the data from the transmitted beams detected by the transmitted beam photosensor 35 and the data measured by the photo-sensors 26a, 26b, which receive the diffracted beams or the scattered beams of the monochrome beams M, are further compensated on the basis of the data from the transmitted beams detected by the transmitted beam photosensor 38.

Figure 4:
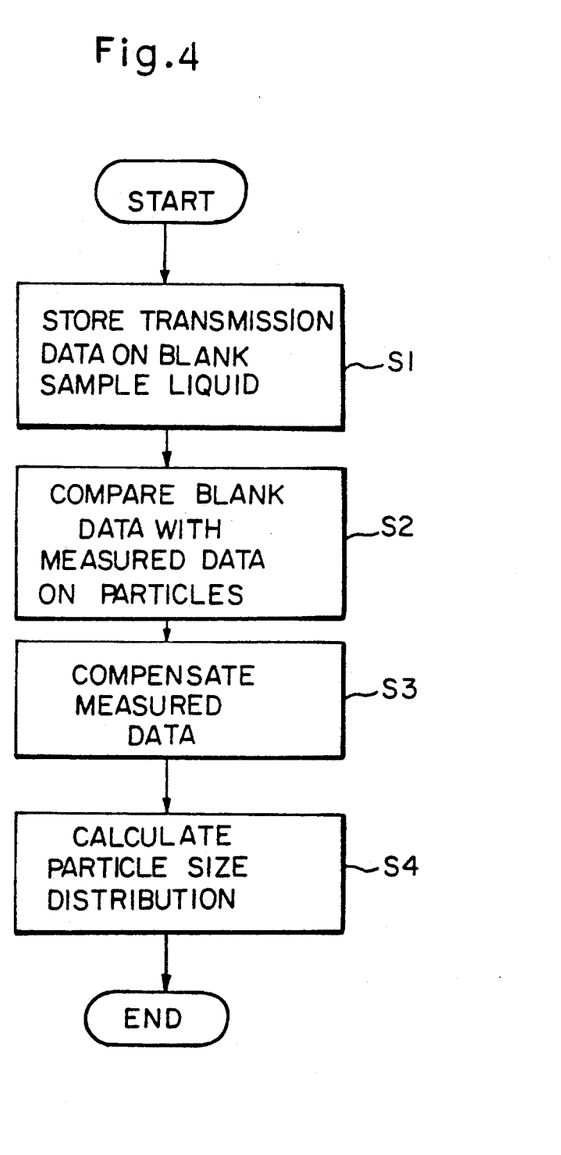
FIG. 4 is a flow chart showing a measuring operation in the apparatus for measuring a particle size distribution.

FIG. 4 is a flow chart showing an outline of the operation conducted in the operating device 40. The measuring procedures of the particle size distribution in the apparatus for measuring a particle size distribution will be below described with reference also to a flow chart shown in FIG. 4.

In the optical system composing the laser beam-emitting means 22, the laser beams L from the laser light source 27 are expanded into a bundle of beams by the beam expander 28 and then are incident upon the sample cell 21. The laser beams L are diffracted or scattered by the sample particles within the sample cell 21 and the diffracted beams or the scattered beams are focused into an image on the ring-shaped detector 25 by means of the collecting lens 24.

In the ring-shaped detector 25, the optical intensity of the laser beams L, transmitting through the sample cell 21 without being diffracted or scattered by the sample particles, is measured by means of the transmitted beam photosensor 35, positioned at a center of the ring-shaped detector 25. In addition, the optical intensity of the laser beams L, diffracted or scattered by the sample particles, is measured by means of the other photosensors 25a, 25b, arranged on the outer circumference of the transmitted beam photosensor 35. Of the respective photosensors 25a, 25b, the photosensors on the outer circumferential side receive the laser beams L scattered at larger scattering angles, while the photosensors on the inner circumferential side receive the laser beams L scattered at smaller scattering angles. Accordingly, the optical intensity detected by means of the photosensors on the outer circumferential side reflect a quantity of the sample particles having larger particle diameters, while the optical intensity detected by means of the photosensors on the inner circumferential side reflect a quantity of the sample particles having smaller particle diameters. The optical intensities detected by means of the respective photosensors 25a, 25b, and 35 are converted into analog electric signals and forwarded to the multiplexer 37 through the amplifiers 36.

In the optical system composing the monochrome beam-emitting means 23, the lamp light from the lamp light source 29 is turned into parallel beams by means of the collimator lens 32 through the aperture 31 and the parallel beams are subsequently turned into the monochrome beams M by means of the interference filter 33. In addition, the monochrome beams M are contracted into a bundle of beams by means of the aperture 34 and then are incident upon the sample cell 21.

The monochrome beams M are diffracted or scattered by the sample particles within the sample cell 21 and the scattered beams are collected by means of the respective corresponding photosensors 26a, 26b through the respective collecting lenses 39a, 39b, followed by measuring the optical intensity distribution by the group of photosensors 26.

In the group of photosensors 26, the photosensors arranged closer to the rear of the sample cell 21 receive those monochrome beams M having larger scattering angles, while the photosensors arranged closer to the front of the sample cell 21 receive the monochrome beams M having smaller scattering angles. Accordingly, an optical intensity detected by the photosensors arranged in the rear of the sample cell 21 reflects the quantity of the sample particles having smaller particle diameters, while an optical intensity detected by means of the photosensors arranged in the front of the sample cell 21 reflects the quantity of the sample particles having larger particle diameters. The optical intensities detected by means of the respective photosensors 26a, 26b, and 38 are converted into analog electric signals and put in the multiplexer 37 through the amplifiers 36.

Since the wavelength range of the lamp light source 29 is purposely selected so as to be shorter than the wavelength of the laser beams L, as described above, the diffracted or scattered single wavelength beams M are effective for the determination of the particle size distribution of the sample particles having smaller particle diameters. On the other hand, the diffracted or scattered laser beams L are effective for the determination of the particle size distribution of the sample particles having larger particle diameters.

The measurement data sent from the respective photosensors, such as 25a, 25b, 35, 26a, 26b, and 38, in short, the analog electric signals, are taken into the multiplexer 37 in a predetermined appointed order. For example, the measurement data is taken first from the photosensors 25a, 25b, etc., and then from the photosensors 26a, 26b, etc..

In addition, in the monochrome beam-emitting means 23, the monochrome beams M, incident upon the sample cell 21 are switched in wavelength by shifting the position of the interference filter 33, either up or down, so that data ranging over several stages of particle diameter can be obtained as data measured by the smaller diameter particle-detecting optical system 20 in this switching-over operation.

The analog electric signals taken in the multiplexer 37 are turned into series signals and then converted into digital signals in turn in the A/D convertor 39, followed by being forwarded to the operating device 40. Alternatively, the data can be addressed and stored in a memory (not shown) for subsequent processing.

The data of the respective transmitted beams measured by means of the transmitted beam photosensors 35, 38 are memorized in the operating device 40 prior to the calculation of the particle size distribution under a calibration condition wherein a sample liquid containing no sample particle (hereinafter referred to as a blank sample liquid as occasion demands) is housed in the sample cell 21, as shown in FIG. 4 (step S1). Upon initialization, the computer program can check appropriate flags to determine the application of power to the necessary components and to remove any previously stored data in the memory to prepare for a calibration procedure. In addition, the data of the transmitted monochrome beams M are separately measured to be memorized for every wavelength switched over by means of the interference filter 33.

In the following calculation of the particle size distribution, the respective data of the transmitted beams measured by the transmitted beam photosensor 38 receiving the transmitted monochrome beams M, transmitted through the sample liquid containing the sample particles within the sample cell 21 and the transmitted beam photosensor 35 receiving the laser beams L transmitting through the sample liquid containing the sample particles within the sample cell 21, are compared with the respective data of the transmitted beams for the blank sample liquid previously memorized (step S2).

That is to say, a transmissivity of the monochrome beams M is calculated from a ratio of the data of the transmitted beams measured by means of the transmitted beam photosensor 35 to the data of the transmitted beams for the corresponding blank sample liquid and similarly a transmissivity of the laser beams L is calculated from a ratio of the data of the transmitted beams measured by the transmitted beam photosensor 38 to the data of the transmitted beams for the corresponding blank sample liquid.

Subsequently, the data measured by means of the photosensors 25a, 25b in the ring-shaped detector 25 are compensated by a quantity corresponding to the transmissivity calculated from the data measured by the transmitted beam photosensor 35. Similarly, the data measured by the photosensors 26a, 26b are compensated by a quantity corresponding to the transmissivity calculated from the data measured by the transmitted beam photosensor 38 (step S3).

Then, the particle size distribution of the sample particles is determined on the basis of the data of measurement of the respective optical intensities compensated in he above describe manner (step S4). Its calculating procedure is carried out on the basis of the theory of the Fraunhofer diffraction or the Mie scattering.

Figure 5:
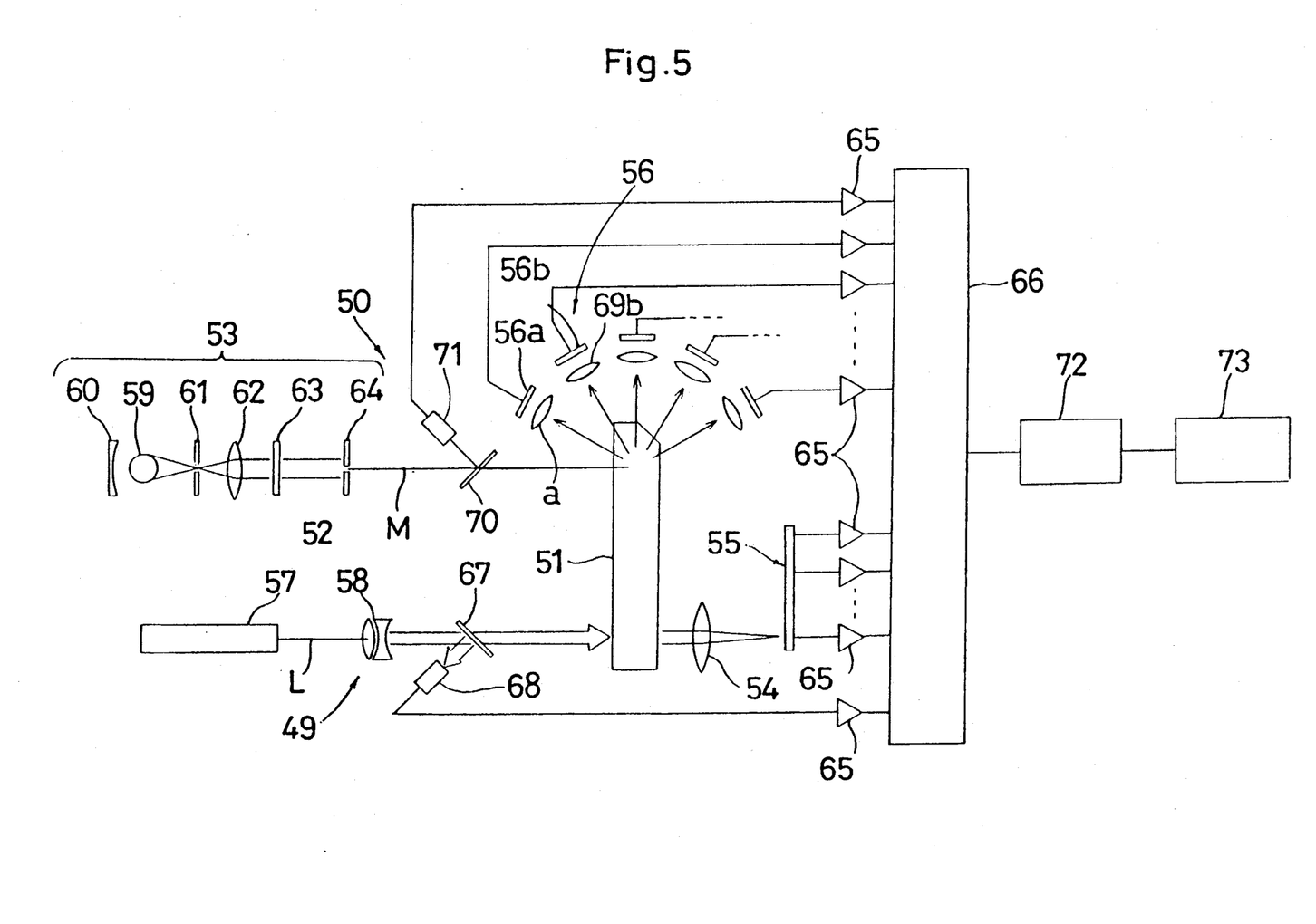
FIG. 5 is a diagram schematically showing an outline of an apparatus for measuring a particle size distribution.

FIG. 5 is a diagram showing an optical measuring system in a apparatus for measuring a particle size distribution according to a second embodiment. A sample cell 51 is a transparent vessel housing a sample liquid with sample particles dispersed in a medium therein and laser beam-emitting means 52 is an optical system for irradiating the sample cell 51 with parallel laser beams L. The laser beam-emitting means 52 is composed of a laser beam source 57 for emitting the parallel laser beams L and a beam expander 58 for expanding a bundle of laser beams L.

A collecting lens 54 for collecting the laser beams L diffracted or scattered by the sample particles on a ring-shaped detector 55 is arranged on an optical axis of the laser beam-emitting means 52 in front of the sample cell 51. The ring-shaped detector 55 is arranged in front of the collecting lens 54 for receiving the laser beams having relatively smaller scattering angles of the laser beams L, diffracted or scattered by the sample particles, to measure their optical intensities.

Figure 6:
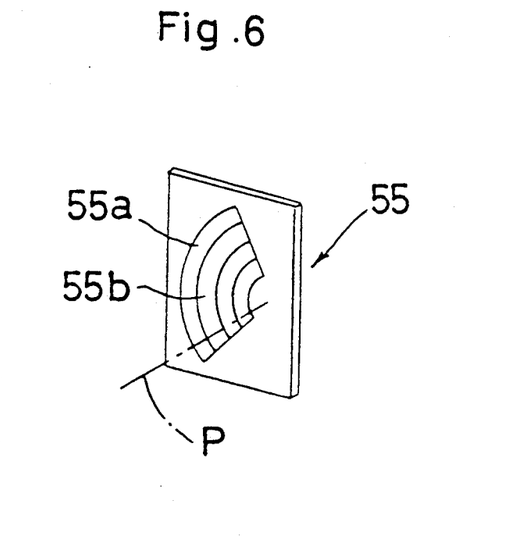
FIG. 6 is a perspective view showing a ring-shaped detector used in the apparatus for measuring a particle size distributic shown in FIG. 5.

FIG. 6 is a perspective view showing a construction of the ring-shaped detector 55. This ring-shaped detector 55 is composed of a plurality of scattered beam photosensors 55a, 55b, arranged so as to be divided into a ring shape with the optical axis P of the laser beam-emitting means 52 as a center for detecting the laser beams L diffracted or scattered by the sample particles at the respective angles, depending upon particle diameters the sample particles. The respective photosensors 55a, 55b of the ring-shaped detector 55 are connected with a multiplexer 66 through respective amplifiers 65.

The laser beam-emitting means 52, the collecting lens 54 and the ring-shaped detector 55 compose a large diameter particle-detecting optical system 49 for receiving the laser beams diffracted or scattered by the sample particle shaving relatively large particle diameters.

A first beam-splitter 67, composed of a half mirror for separating a portion of the laser beams L, irradiated through the expander 58, is disposed on the optical axis of the laser beam-emitting means 52 between the beam expander 58 and the sample cell 51. The part of the laser beams L separated by means of its beam-splitter 68 is received by a first monitor photosensor 68. Also, the monitor photosensor 68 is connected with the multiplexer 66 through a corresponding amplifier 65.

The monochrome light-emitting means 53 is an optical system for irradiating the sample cell 61 with monochrome light M having wavelengths shorter than those of the laser beams L and is composed of a lamp light source 59, a spherical mirror 60, apertures 61, 64, a collimator lens 62, and an interference filter 63. The spherical mirror 60 is a mirror for collecting light emitted backward from the lamp light source 69 on the aperture 61 arranged in front of the lamp light source 59. The aperture 61 contracts the light from the lamp light source 59 to form a sufficiently small bundle of beams. A collimator lens 62, arranged in front of the aperture 61, is a lens for converting the lamp light, which has been contracted by means of the aperture 61, into parallel beams. The interference filter 63, arranged in front of the collimator lens 62, is a filter for taking out beams M, having an appointed monochrome range from the parallel beams.

The aperture 64, arranged in front of the interference filter 63, provides a contraction of a bundle of the monochrome beams M from the interference filter 63. The monochrome beams M, which have passed through the aperture 64, are incident upon a position different from the incident position of the laser beams L of the sample cell 51.

In addition, a plurality of photosensors, such as elements 56a, 56b, composing a group of photosensors 56 for individually detecting the monochrome beams M having relatively larger scattering angles of the monochrome beams M, diffracted or scattered by the sample particles for various scattering angles, are arranged at the respective scattering angle positions. In particular, the photosensc s 56a, 56b are arranged not only on a side in the rear of the sample cell 61, that is, the side on which the single wavelength-emitting means 53 is arranged, but also on a side in front of the sample cell 51 to measure the optical intensity for the monochrome beams M, scattered ahead of the sample cell 51.

The respective photosensors 56a, 56b, etc., receive the respective diffracted or scattered beams collected by the collecting lenses 59a, 59b, corresponding thereto. The collecting lenses 56a, 56b are connected with the multiplexer 66 through respective amplifiers 65, corresponding thereto.

The above described monochrome light-emitting means 53, the group of photosensors 56 and the collecting lens 69a, 69b compose a smaller diameter particle-detecting optical system 50 for receiving the monochrome light, diffracted or scattered by the sample particles having relatively smaller particle diameters.

In addition, a second beam-splitter 70, composed of a half mirror or the like, for separating a part of the monochrome beams M irradiated through the aperture 64, is disposed on the optical axis of the monochrome beam-emitting means 52 between the aperture 64 and the sample cell 51 so that a part of the monochrome beams M, separated by the beam-splitter 70, may be received by a second monitor photosensor 71. Also, the monitor photosensor 71 is connected with the multiplexer 66 through a corresponding respective amplifier 65.

The multiplexer 66 is a circuit having a function of taking in data of optical intensity detected by the respective photosensors 55a, 55b of the ring-like detector 55, data detected by the respective photosensors 56a, 56b of the group of photosensors 56 and data detected by the monitor photosensors 68, 71 in an appointed order and converting the data into series signals to send them to an A/D converter 72. The A/D convertor 72 is a circuit for converting the data of measurement, analog data, into digital data and the digital data is sent to an operating device 73.

The operating device 73 is a device for conducting a computational operation of determining a particle size distribution of the sample particles within the sample cell 51 on the basis of the digital data on optical intensity and can compose a computer and appropriate software programs. This computational operation determines the particle size distribution on the basis of the theory of the Fraunhofer diffraction or the Mie scattering, but also includes a preliminary compensating function for compensating the input data used in the operation prior to the computation operation of particle size distribution determination.

The compensation operation in this case compensates the data of optical intensity detected by the photosensors 55a, 55b, 56a, 56b on the basis of data of the laser beams L and the monochrome beams M, initially measured by the respective monitor photosensors 68, 71 at a specific point of time when the diffracted beams or the scattered beams are also received by the respective photosensors 55a, 55b and 56a, 56b. The data measured by the photosensors 55a, 55b, which receives the diffracted beams or the scattered beams of the laser beams L, are compensated on the basis of the data detected by the monitor photosensor 68, and the data measured by the photosensors 56a, 56b, which receives the diffracted beams or the scattered beams of the monochrome beams M, are compensated on the basis of the data detected by means of the monitor photosensor 71, respectively.

Figure 7:
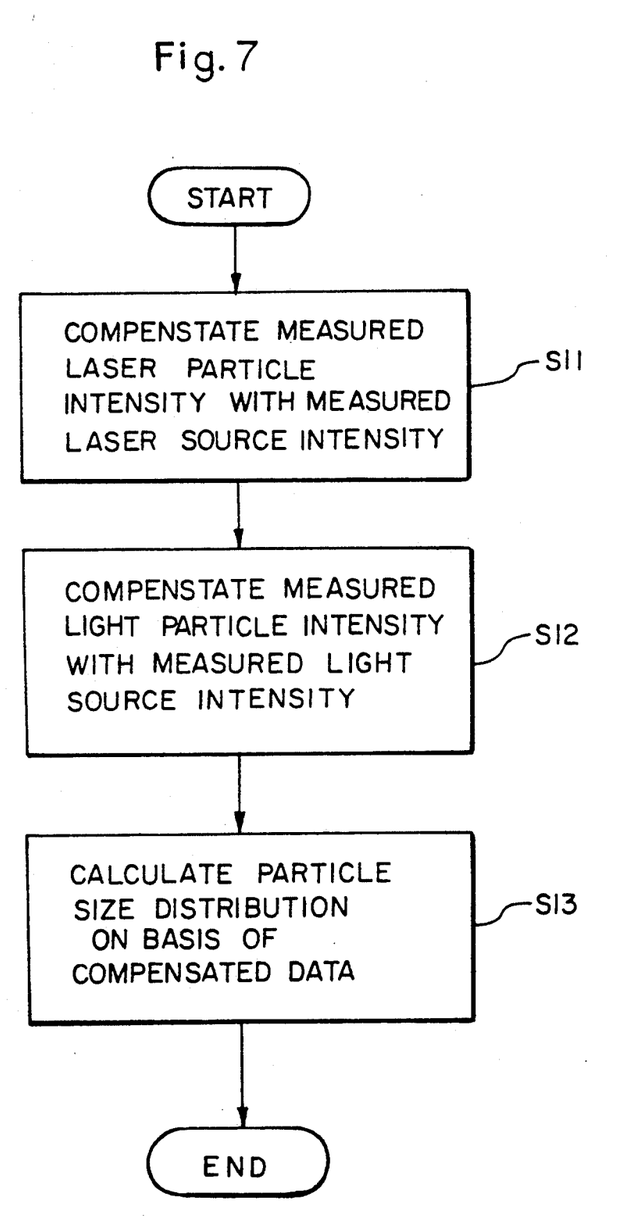
FIG. 7 is a flow chart showing a measuring operation in the apparatus for measuring a particle size distribution.

FIG. 7 is a flow chart showing a schematic flow chart outline of the calibration operation conducted in the operating device 73. The measuring procedures of the particle size distribution will be described with reference also to the flow chart shown in FIG. 7.

In the optical system comprising the laser beam-emitting means 52, the laser beams L from the laser light source 57 are expanded in a bundle of beams by the beam expander 58, and a part of them transmits through the first beam-splitter 67 to be incident upon the sample cell 51.

The laser beams L are diffracted or scattered by the sample particles within the sample cell 51, and the diffracted beams or the scattered beams are focused onto an image on the ring-shaped detector 55 by the collecting lens 54. The optical intensity of the laser beams L, diffracted or scattered by the sample particles, is measured by means of the photosensors 55a, 55b, arranged in the ring-shaped detector 55. Of the respective photosensors 55a, 55b, the photosensors on the outer circumferential side receive the laser beams L scattered at larger scattering angles, while the photosensors on the inner circumferential side receive the laser beams L scattered at smaller scattering angles. Accordingly, the optical intensity detected by the photosensors on the outer circumferential side represents a quantity of the sample particles having larger particle diameters, while the optical intensity detected by the photosensors on the inner circumferential side represents an quantity of the sample particles having smaller particle diameters.

In addition, a part of the laser beams L coming from the beam expander 58 and separated by the first beam-splitter 67 is received by the first monitor photosensor 68. The optical intensities detected by the respective photosensors 55a, 55b, 68 are converted into analog electrical signals and put into the multiplexer 66 through the amplifiers 65.

In the optical system composing the monochrome beam-emitting means 53, the lamp light from the lamp light source 59 is turned into parallel beams by the collimator lens 62 through the aperture 61 and the parallel beams are filtered into the monochrome beams M by means of the interference filter 63. In addition, the monochrome beams M are contracted into bundles of beams by the aperture 64 and then a part of them becomes incident upon the sample cell 51.

The monochrome beams M are diffracted or scattered by the sample particles within the sample cell 51 and the scattered beams are collected by the respective corresponding photosensors 56a, 56b through the respective collecting lenses 69a, 69b, followed by measuring the optical intensity distribution by the group of photosensors 56.

In the group of photosensors 56, these photosensors arranged closer to the rear of the sample cell 51, receive the monochrome beams M, having the larger scattering angles, while the photosensors arranged closer to the front of the sample cell 51 receive the monochrome beams M, having smaller scattering angles. Accordingly, an optical intensity detected by the photosensors arranged in the rear of the sample cell 51 represents the quantity of the sample particles having smaller particle diameters, while an optical intensity detected by the photosensors arranged in the front of the sample cell 51 represents the quantity of the sample particles having larger particle diameters. In addition, a portion of the monochrome beams M passing through the aperture 64 of the monochrome-emitting means 53 and separated by means of the second beam-splitter 70, is received by the second monitor photosensor 68.

The optical intensities detected by means of the respective photosensors 56a, 56b, and 71 are converted into analog electric signals and applied to the multiplexer 66 through the amplifiers 65.

Since the wavelength range of the lamp light source 59 is selected so as to be shorter than the wavelength of the laser beams L, as above described, the diffracted or scattered monochrome beams M are effective for the determination of particle size distribution of the sample particles having smaller particle diameters. On the other hand, the diffracted or scattered laser beams L are effective for the determination of the particle size distribution of the sample particles having larger particle diameters The data of measurement sent from the respective photosensors 55a, 55b, and 68, 56a, 56b, and 71, in short, the analog electric signals, are taken into the multiplexer 56 in a predetermined order. That is to say, for example, the data of measurement are taken in order from the photosensors 56a, 56b, corresponding to the sample particles having smaller particle diameters to the photosensors 55a 55b, corresponding to the sample particles having larger particle diameters.

The analog electric signals inputted into the multiplexer 66 are turned into series signals and then converted into digital signals in the A/D convertor 71 and applied to the operating device 73.

In the operating device 73, a procedure (step S11) of compensating the data measured by means of the ring-shaped detector 55 on the basis of data measured by the first monitor photosensor 68 at the same point in measurement time and a procedure (step S12) of compensating the data measured by the group of photosensors 56 on the basis of the data measured by the second monitor photosensor 71, also at the same point of measuring time are conducted prior to the actual calculation of the particle size distribution, as shown by a flow chart in FIG. 7. The data measured by the ring-shaped detector 55 are either increased or decreased by a compensation technique, depending upon an increase or decrease of the quantity of light received by the first monitor photosensor 68, in short, a fluctuation of the laser beams L in quantity of light, and the data measured by the group of photosensors 56 are either increased or decreased by a compensation technique, depending upon an increase or decrease of the quantity of light received by the second monitor photosensor 71, in short, a fluctuation of the monochrome beams M in quantity of light.

Subsequently, a particle size distribution of the sample particles is determined on the basis of the data of measurement of the respective optical intensities compensated in the above described manner (step S13). This calculating procedure is conducted on the basis of the theory of the Fraunhofer diffraction or the Mie scattering.

According to the first embodiment of the present invention, the data measured by the ring-shaped detector for measuring the optical intensity of the laser beams , diffracted or scattered by the sample particles and the data measured by the group of photosensors measuring the optical intensity of the single wavelength beams, are compensated by a quantity depending upon the concentration of the sample particles at that time and the particle size distribution of the sample particles is calculated by the particle size distribution-calculating means on the basis of the compensated data of measurement, so that an accurate particle size distribution can be measured without being influenced by a multiple scattering effect.

According to the second embodiment of the present invention, the data measured by the ring-shaped detector for measuring the optical intensity of the laser beams, diffracted or scattered by the sample particles and the data measured by the group of photosensors for measuring the optical intensity of the single wavelength beams, are compensated by a quantity depending upon the optical intensity of the laser beams and the monochrome beams measured by the first monitor photosensor and the second monitor sensor, respectively, at the same point of measuring time and the particle size distribution of the sample particles is calculated by the particle size distribution-calculating means on the basis of the compensated data of measurement, so that an accurate particle size distribution can be measured without being influenced by the fluctuation of the light source on the quantity of light.

In addition, the data measured by the larger particle diameter particle-detecting optical system and the data measured by the smaller particle diameter particle-detecting optical system are taken in by a multiplexing technique to be used as the data for the particle size distribution-calculating means, os that a wide range of particle size distributions, ranging from the small particle diameters to the large particle diameters, can be simply measured, at one time. Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An apparatus for measuring a wide range of particle sizes in a sample fluid comprising:

first means for irradiating the sample fluid with a first light source along a first predetermined optical axis;

second means for irradiating the sample fluid with a second light source having a different wavelength than the first light source along a second predetermined optical axis;

first detector means for measuring the optical intensities of the first light source after interaction with the particles in the sample fluid at predetermined angles off the first optical axis;

second detector means for measuring the optical intensities of the second light source after interaction with the particles in the sample fluid at predetermined angles off the second optical axis;

means for measuring a transmission characteristic of the first light through the sample fluid without particles and providing a representative signal;

means for measuring a transmission characteristic of the second light through the sample fluid without particles and providing a representative signal;

means for adjusting the measured optical intensities of the first detector means in response to the representative signal to provide compensated data of the first light source intensities;

means for adjusting the measured optical intensities of the second detector means in response to the representative signal to provide compensated data of the second light source intensities, and means for calculating the particle size distribution in the sample fluid from the respective compensated first and second data of the light source intensities.

2. The invention of claim 1 wherein the first means for irradiating the sample fluid includes a laser light source.

3. The invention of claim 1 wherein the second means for irradiating the sample fluid includes an interference filter capable of providing different wavelengths of irradiating light.

4. The invention of claim 1 wherein the means for calculating includes a computer and a program to calculate particle size based on a Fraunhofer diffraction theory.

5. An apparatus for measuring a wide range of particle sizes in a sample fluid comprising:
   first means for irradiating the sample fluid with a first light source along a first predetermined optical axis;
   second means for irradiating the sample fluid with a second light source having a different wavelength than the first light source along a second predetermined first optical axis;
   first detector means for measuring the optical intensities of the first light source after interaction with the particles in the sample fluid at predetermined angles off the optical axis at predetermined angles off the second optical axis;
   second detector means for measuring the optical intensities of the second light source after interaction with the particles in the sample fluid;
   means for measuring the intensity of the irradiating first light source simultaneously with the measurement of the first detector and providing a
   means for measuring the intensity of the irradiating second light source simultaneously with the measurement of the second detector and providing a representative signal;
   means for compensating the first detector measured optical intensities with the representative signal of the first light source;
   means for compensating the second detector measured optical intensities with the respective signals of the second light source, and
   means for calculating the particle size distribution in the sample fluid based on the compensated first and second measured light intensities.

6. In an apparatus for measuring particle size distribution comprising a larger diameter particle-detecting optical system containing a laser beam-irradiating means for irradiating a sample vessel, in which a medium with sample particles are dispersed with laser beams and a ring-shaped detector for measuring optical intensities of laser beams having respective scattering angles diffracted or scattered by said sample particles and a smaller particle-detecting optical system containing a monochrome light-irradiating means for irradiating said sample vessel with monochrome light and a group of photosensors for measuring optical intensities of said monochrome light having the respective scattering angles diffracted or scattered by the sample particles, the improvement comprising:
   a first transmitted beam-measuring photosensor for measuring an optical intensity of a laser beam transmitting through the sample vessel without being diffracted or scattered by the sample particles;
   a second transmitted beam-measuring photosensor for measuring an optical intensity of a monochrome light transmitting through the sample vessel without being diffracted or scattered by the sample particles;
   compensating means for calculating a transmission factor of said light and that of said monochrome light beam, respectively, on the basis of the data measured by means of said first transmitted beam-measuring photosensor and said second transmitted beam-measuring photosensor to compensate the data measured by means of said ring-shaped detector and said group of photosensors by a quantity corresponding to said transmission factors, and
   particle size distribution-calculating means for calculating a particle size distribution of the sample particles from the compensated data of measurement on the basis of a theory of the Fraunhofer diffraction or the Mie scattering.

7. In an apparatus for measuring a particle size distribution, including a large diameter particle-detecting optical system containing light-irradiating means for irradiating a sample vessel, in which a medium with sample particles are dispersed, with a laser beam and a detector for measuring optical intensities of laser beams having respective scattering angles diffracted or scattered by said sample particles and a smaller particle-detecting optical system containing monochrome light-irradiating means for irradiating said sample vessel with monochrome light and a group of photosensors for measuring optical intensities of monochrome light having respective scattering angles diffracted or scattered by the sample particles, the improvement comprising:
   a first beam splitter for separating a portion of the laser beams before they are incident upon the sample vessel;
   a first monitoring photosensor for measuring an optical intensity of the laser beams separated by said first beam splitter;
   a second beam splitter for separating a portion of the monochrome light before it is incident upon the sample vessel;
   a second monitoring photosensor for measuring an optical intensity of the monochrome light separated by said second beam splitter;
   means for receiving data measured by means of said ring-shaped detector, data measured by means of said group of photosensors, and data measured by means of said respective monitoring photosensors;
   compensating means for compensating said data measured by means of the ring-shaped detector and the group of photosensors depending upon said data measured by the respective monitoring photosensors at the same point of time as when the above described data are measured, and
   particle size distribution-calculating means for particles from the compensated data of measurement on the basis of a theory of the Fraunhofer diffraction or the Mie scattering.

* * * * *